United States Patent [19]

Agrawal et al.

[11] Patent Number: 6,114,129
[45] Date of Patent: Sep. 5, 2000

[54] METHODS OF DETECTING T-CELL ACTIVATION AND TREATING DISORDERS ASSOCIATED WITH T-CELL DYSFUNCTION

[75] Inventors: Babita Agrawal; B. Michael Longenecker, both of Alberta, Canada

[73] Assignee: Biomira, Inc., Edmonton, Canada

[21] Appl. No.: 09/339,944

[22] Filed: Jun. 25, 1999

Related U.S. Application Data

[60] Provisional application No. 60/090,916, Jun. 26, 1998.

[51] Int. Cl.[7] .......................... G01N 33/53; G01N 33/555; G01N 33/567; G01N 33/542; C12Q 1/02
[52] U.S. Cl. .......................... 435/7.24; 435/7.9; 435/29; 530/387.1; 424/154.1; 424/130.1
[58] Field of Search ............................... 424/154.1, 130.1; 530/387.1; 435/7.9, 7.24, 29

[56] References Cited

U.S. PATENT DOCUMENTS

| | | |
|---|---|---|
| 5,527,891 | 6/1996 | Koganty et al. . |
| 5,744,144 | 4/1998 | Finn et al. . |

OTHER PUBLICATIONS

Krishna et al.; "9–0–Acetylation of Sialomucins: A Novel Marker of Murine CD4 T Cells That Is Regulated During Maturation and Activation", J. Exp. Med., 185:11 (1997).
Agrawal et al.; "Cancer–associated MUC1 mucin inhibits human T–cell proliferation, which is reversible by IL–2", Nature Medicine 43–49 (1998).
Agrawal et al., "Expression of MUC1 Mucin on Activated Human T Cells: Implications for a Role of MUC1 in Normal Immune Regulation" Cancer Research 4079–4081 (1998).
Agrawal et al.; "The biological role of mucins in cellular interactions and immune regulation: prospects for cancer immunotherapy" Molecular Medicine Today 379–403 (1998).
Agrawal et al., Nature Med. 4:43 (1998).
Ligtenberg et al., Cancer Res. 52: 2318 (1992).
Wesseling et al., J. Cell Biol. 129:255 (1995).
Wesseling et al., Mol. Biol. Cell 7:565 (1996).
Pemberton et al., "Antibodies to the cytoplasmic domain of the MUC1 mucin show conservation throughout mammals" Biochem. Biophys. Res. Comm. (USA) 185:167 (1992).
Fontenot et al., "Biophysical Characterization of One–, Two–, and Three–Tandem Repeats of Human Mucin (muc–1) Protein Core" Cancer Research 53:5386 (1993).

*Primary Examiner*—Christina Y. Chan
*Assistant Examiner*—Gerald R. Ewoldt
*Attorney, Agent, or Firm*—Foley & Lardner

[57] ABSTRACT

Methods of detecting activated T-cells involve monitoring levels of MUC-1 mucin expression at the protein and/or mRNA level. Compositions for modulating immune function contain compounds that modulate the expression or function of MUC-1. Methods of treating disorders associated an inappropriate state of T-cell activation involve contacting a T-cell with a compound containing an inhibitor of MUC-1 expression or function.

5 Claims, 3 Drawing Sheets

A. CULTURE IN THE ABSENCE OF PHA:

B. CULTURE IN THE PRESENCE OF MITOGEN PHA

N.B. ISOTYPE MATCHED ANTIBODY WAS USED AS CONTROLS.

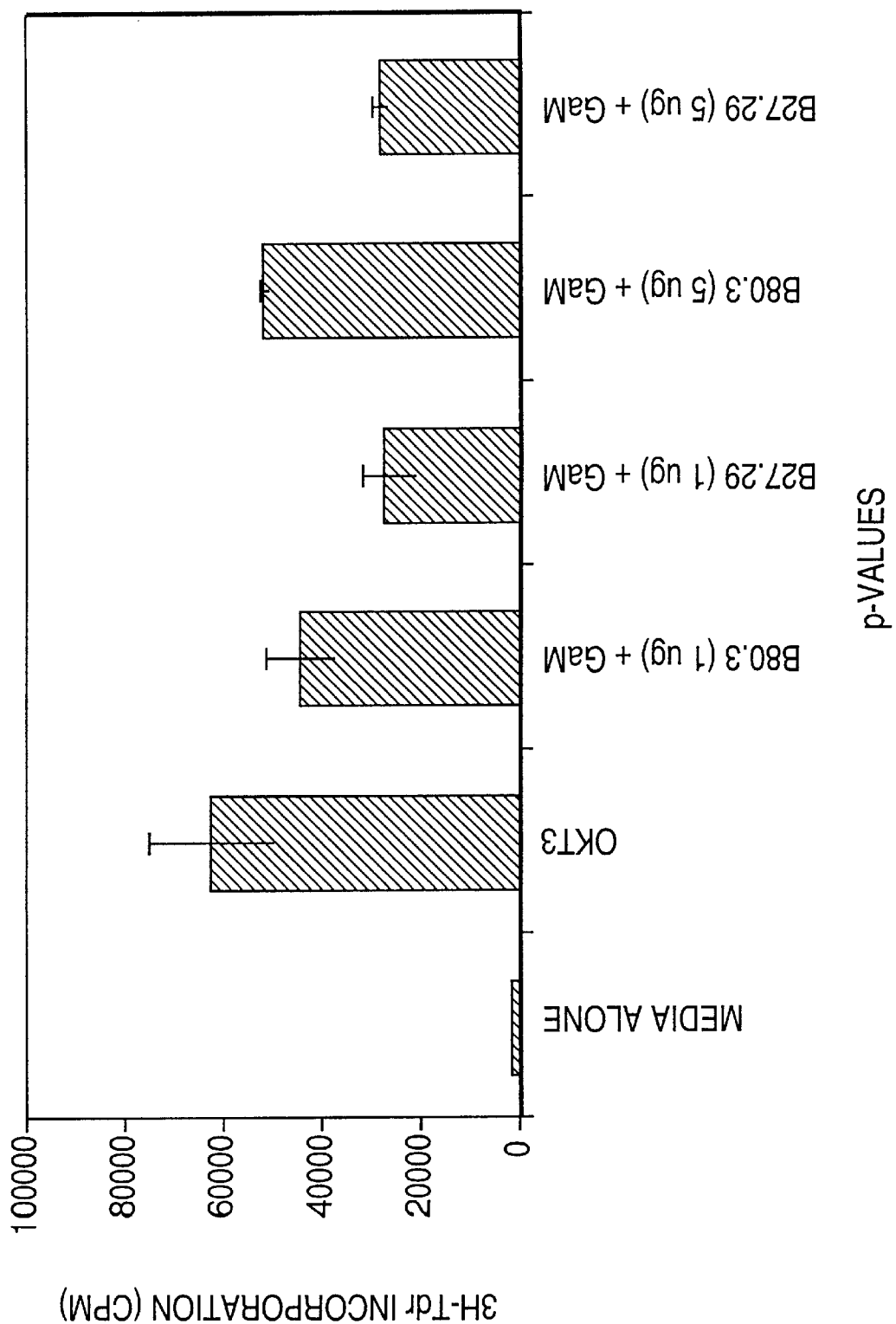

SEQUENCE LISTING

```
<160> NUMBER OF SEQ ID NOS: 11

<210> SEQ ID NO 1
<211> LENGTH: 20
<212> TYPE: PRT
<213> ORGANISM: Homo sapiens

<400> SEQUENCE: 1

Pro Asp Thr Arg Pro Ala Pro Gly Ser Thr Ala Pro Pro Ala His Gly
 1               5                   10                  15

Val Thr Ser Ala
            20

<210> SEQ ID NO 2
<211> LENGTH: 4
<212> TYPE: PRT
<213> ORGANISM: Homo sapiens

<400> SEQUENCE: 2

Asp Thr Arg Pro
 1

<210> SEQ ID NO 3
<211> LENGTH: 7
<212> TYPE: PRT
<213> ORGANISM: Homo sapiens

<400> SEQUENCE: 3

Ser Ala Pro Asp Thr Arg Pro
```

```
                       1               5

<210> SEQ ID NO 4
<211> LENGTH: 5
<212> TYPE: PRT
<213> ORGANISM: Homo sapiens

<400> SEQUENCE: 4

Gly Val Thr Ser Ala
 1               5

<210> SEQ ID NO 5
<211> LENGTH: 4
<212> TYPE: PRT
<213> ORGANISM: Homo sapiens

<400> SEQUENCE: 5

Pro Arg Thr Asp
 1

<210> SEQ ID NO 6
<211> LENGTH: 20
<212> TYPE: PRT
<213> ORGANISM: Homo sapiens

<400> SEQUENCE: 6

Gly Val Thr Ser Ala Pro Asp Thr Arg Pro Ala Pro Gly Ser Thr Ala
 1               5                  10                  15

Pro Pro Ala His
             20

<210> SEQ ID NO 7
<211> LENGTH: 16
<212> TYPE: PRT
<213> ORGANISM: Homo sapiens

<400> SEQUENCE: 7

Gly Val Thr Ser Ala Pro Asp Thr Arg Pro Ala Pro Gly Ser Thr Ala
 1               5                  10                  15

<210> SEQ ID NO 8
<211> LENGTH: 6
<212> TYPE: PRT
<213> ORGANISM: Homo sapiens

<400> SEQUENCE: 8

Ala Pro Asp Thr Arg Pro
 1               5

<210> SEQ ID NO 9
<211> LENGTH: 10
<212> TYPE: PRT
<213> ORGANISM: Homo sapiens

<400> SEQUENCE: 9

Thr Ser Ala Pro Asp Thr Arg Pro Ala Pro
 1               5                  10

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 10
tctactctgg tgcacaacgg                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11
ttatatcgag aggctgcttc c                                            21
```

METHODS OF DETECTING T-CELL ACTIVATION AND TREATING DISORDERS ASSOCIATED WITH T-CELL DYSFUNCTION

This application claims the benefit of U.S. Provisional Application, Ser. No. 60/090,916, filed Jun. 26, 1998.

BACKGROUND OF THE INVENTION

Mucins are large (>200 kDa) glycoproteins with a high carbohydrate content (50–90% by weight) expressed by a variety of normal and malignant epithelial cells (Strous el al., Crit. Rev. Biochem. Mol. Biol. 27:57 (1992); Devine et al, BioEssays 14:619 (1992)). Among the human mucins, MUC-1 is unique in its cell surface transmembrane expression (Gendler et al., J. Biol. Chem. 265:15286 (1990); Siddiqui et al Proc. Natl. Acad. Sci. USA 85:2320 (1988); Gendler et al, Proc. Natl. Acad. Sci. USA 84:6060 (1987); Ligtenberg et al., J. Biol. Chem. 265:5573 (1990)).

MUC-1 mucin contains a polypeptide core consisting of 30–100 repeats of a 20 amino acid sequence (Gendler et al, J. Biol. Chem. 265:15286 (1990). The presence of large amounts of oligosaccharides attached along the length of the polypeptide core of MUC-1 mucin enhances its rigidity, resulting in large flexible rod-like molecules that may extend several hundred nanometers from the apical epithelial cell surface into the lumens of ducts and glands (Bramwell et al., J. Cell Sci. 86:249 (1986)).

Adenocarcinoma patients with elevated serum MUC-1 mucin levels have higher numbers of T-cells expressing CD69, an early activation marker, than the patients with normal serum MUC-1 levels (Reddish et al., Cancer Immunol. Immunother. 42:303 (1996); Bowen-Yacyshyn et al., Int. J. Cancer 61:470 (1995). It was hypothesized that patients with high serum MUC-1 levels and high numbers of $CD69^+$ peripheral blood T-lymphocytes were in a state of T-cell anergy (Reddish et al, Cancer Immunol. Immunother. 42:303 (1996)) similar to tumor infiltrating lymphocytes (TILs), which are $CD69^+$ but appear to be "frozen" in an early activation state and unable to express normal interleukin 2 (IL-2) and IL-2R levels (Alexander et al., J. Immunother. 17:39 (1995); Berd et al., Cancer Immunol. Immunother. 39:141 (1994); Bamd et al, Proc. Natl. Acad. Sci. USA 86:7159 (1989).

Elevated levels of serum MUC-1 are associated with poor survival and a lower anti-cancer immune response of metastatic breast, colorectal and ovarian cancer patients following immunotherapy (Bowen-Yacyshyn et al, 1995 Int. J. Cancer 61:470; MacLean et al, J. Immunother. 20:70 (1997)). Cumulatively, all of these results are consistent with an immunosuppressive role for MUC-1 mucin.

Direct demonstration of an immunosuppressive role of cancer associated MUC-1 mucin came from recent work (Agrawal et al, Nature Med. 4:43 (1998)) showing that cancer associated, affinity purified, MUC-1 mucin and synthetic tandem repeats of MUC-1 polypeptide core inhibited human T-cell proliferative responses to polyclonal stimuli. The degree of inhibition of T-cell proliferation was directly proportional to the number of tandem repeats present on MUC-1 polypeptide core synthetic peptides.

This inhibition was reversible by adding a 16 mer (<1 tandem repeat of the polypeptide core) MUC-1 synthetic peptide (Agrawal et al., Nature Med. 4:43), which confirms the role of the MUC-1 polypeptide core in the inhibition of T-cell responses and suggests an inhibitory mechanism, which involves cross-linking of a T-cell surface molecule. The observation that addition of exogenous IL-2 or anti-CD28 monoclonal antibody (mAb) reversed the cancer associated MUC-1 mucin induced inhibition of T-cell response is consistent with the mechanism of inhibition being anergy (Agrawal et al, Nature Med. 4:43). Our understanding of the immunoregulatory role of cancer associated MUC-1 mucin has revealed some of the intricate mechanisms tumor cells use to regulate immune responses for their enhanced survival.

Aside from direct immmunomodulatory functions, other functions have been proposed for MUC-1 mucin (Gendler et al., Ann. Rev. Physiol. 57:607 (1995)) which involve steric hindrance by the large glycosylated extracellular domain of cell-cell or cell-substratum interactions, remodeling the cytoskeletal network, or by down-regulating the activities of other molecules such as catenins, cadherins or integrins via signal transduction events (Yamamoto et al., J. Biol. Chem. 272.12492 (1997); Parry et al., Exp. Cell Res. 188:302 (1990). Its cytoplasmic tail is phosphorylated consistent with a transmembrane signal transduction function for MUC-1 (Pandey et al., Cancer Res. 55:40003 (1995); Zrihan-Licht et al., FEBS Lett. 356:130 (1994); Mockensturm-Gardner et al., Mol. Biol. Cell 7:434a (1996); Mockensturm-Gardner et al., Proc. Amer. Assn. Cancer Res. 39:375a (1998).

Paradoxically, in previous studies MUC-1 mucin has been proposed to act both as an anti-adhesive as well as an adhesive molecule. The extended conformation of the extracellular domain of MUC-1 mucin may contribute to the anti-adhesive properties, resulting in reduced cell-cell aggregation and decreased adherence to extracellular matrix components in in vitro adhesion assays (Ligtenberg et al, 1992 Cancer Res. 52:2318; Wesseling et al, 1995 J. Cell Biol. 129:255; Wesseling et al., 1996 Mol. Biol. Cell 7:565). Thus, MUC-1 mucin may protect cancer cells from destruction by natural killer or other immune cells (Hayes et al., 1990 J. Immunol. 145:962; Ogata et al., 1992 Cancer Res. 52:4741; Zhang et al., 1997 Cell. Immunol. 66:158; van de Wiel-van Kemenade et al., 1993 J. Immunol. 151:767).

MUC-1 on cancer cells can also have adhesive features as it expresses carbohydrate structures that may be ligands for selectin-like molecules on endothelial cells (Baeckstrom et al., 1991 J. Biol. Chem. 266:21537; Hanski et al., 1993 Cancer Res. 53:4082; Sikut et al., 1996 Int. J. Cancer 66:617; Zhang et al., 1997 Tumor Biol. 18:175; Zhang et al., 1996 J. Cell. Biochem. 60:538). MUC-1 mucin has also been shown to be a ligand for ICAM-1 (Regimbald et al., 1996 Cancer Res. 56:4244), another adhesion molecule involved in cell-cell interactions. MUC-1 can be shed from tumors and detected in serum (Hayes et al., 1985 J. Clin. Invest. 75:1671; Burchell et al., 1984 Int. J. Cancer 34:763; Boshell et al., 1992 Biochem. Biophys. Res. Commun. 185:1; Williams et al., 1990 Biochem. Biophys. Res. Conimun. 170:1331). The presence of soluble MUC-1 has been shown to inhibit adhesive interactions of rnigrating cells with endothelial cells (Zhang et al., 1997 Tumor Biol. 18:175) and thus could cause decreased recruitment of inflammatory cells to the tumor site.

Although it has primarily been studied based on its association with cancer, MUC-1 is in fact expressed by a variety of normal tissues. A number of secretory epithelial cells, for example, express and secrete MUC-1 mucin. Although, this MUC-1 is highly glycosylated, and is therefore somewhat different than cancer-associated MUC-1, which is under glycosylated.

Various glycoforms of MUC-1 mucin (similar to those of cancer associated MUC-1 mucin) have been found to be present in endometrium and in the serum of pregnant women. McGuckin et al., Tumour Biol. 15:33 (1994). During the menstrual cycle, the abundance of MUC-1 varies in human endometrium. Moreover, progesterone up regulates the transcription of MUC-1 and maximum MUC-1 expression appears in the implantation phase. Hey et al., J. Clin. Endocrinol. Metab. 78:337 (1994).

Interestingly, it has been shown that high levels of progesterone present during days 14–28 of the menstrual cycle are associated with inhibition of CTL activity in the uterus. Consequently, the down-regulation of CTL activity may allow implantation of a semi-allogeneic embryo, which would be otherwise be rejected. White et al., J. Immunol. 158:3017 (1997). The mechanism of this T-cell down-regulation, however, is unknown. Indeed, the art is generally deficient in its knowledge regarding T-cell activation and de-activation.

T-cell activation is an indicator of the immune state and thus is useful in monitoring a variety of diseases. For example, certain autoimmune diseases are etiologically linked to T-cell activation. Moreover, the ability to control the state of T-cell activation would, likewise, be useful in treating a wide variety of disorders.

A need exists, therefore, in the art for the elucidation of a fundamental pathway involved in the regulation of T-cell activation. Provided such a pathway, certain diagnostic and medicinal agents will be made available to the art. The present invention, as detailed below, describes such a novel fundamental pathway as well as a variety of compounds for modulating that pathway, which have certain diagnostic and therapeutic applications.

SUMMARY OF THE INVENTION

It is therefore, one object of the invention to provide reagents and methods for determining the state of T-cell activation. According to this aspect of the invention, methods are provided which comprise detecting the amount of MUC-1 expression in a T-cell-containing sample and comparing said amount to a non-activated T-cell-containing control. In one embodiment, detection involves quantifying the amount of MUC-1 expression, preferably by contacting the sample with an antibody which is specific for MUC-1. In another embodiment detecting can be accomplished by contacting the sample with a polynucleotide probe which is capable of specifically detecting a MUC-1-associated nucleotide sequence. In yet another embodiment, methods of ascertaining global immune activation are provided. In a typical method, a sample is provided from a patient and the amount of MUC-1 present in the sample is detected.

It is another object of the invention to provide methods for modulating T-cell activation, generally in the context of therapeutic methods. According to this object, methods are provided which entail treatment with compounds that either promote or antagonize the activity of MUC-1, thus altering the balance of T-cell activation in patients in need of such treatment.

BRIEF DESCRIPTION OF THE DRAWINGS

FIG. 3 demonstrates that antibody cross-linking MUC-1 on the surface of the T-cells down-regulates the proliferative response.

DETAILED DESCRIPTION OF THE INVENTION

Overview

Figure 1:
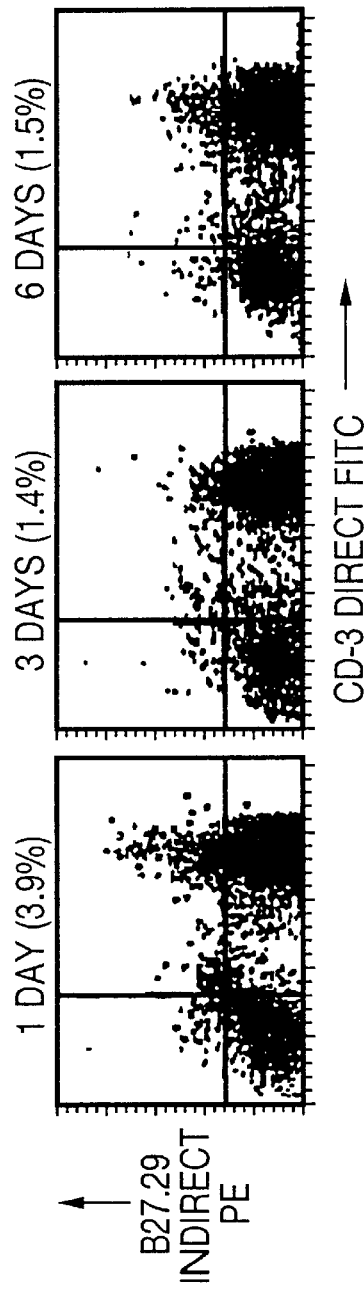
FIG. 1A shows FACS analysis of a time course of MUC-1 expression on activated human T-cells in the absence of mitogen stimulus. The number in parentheses represents percent MUC-1 positive T-cells.
FIG. 1B shows a FACS analysis of a time course of MUC-1 expression on activated human T-cells cultured in the presence of phytohemaglutanin (PHA). The number in parentheses represents percent MUC-1 positive T-cells.
Figure 1:
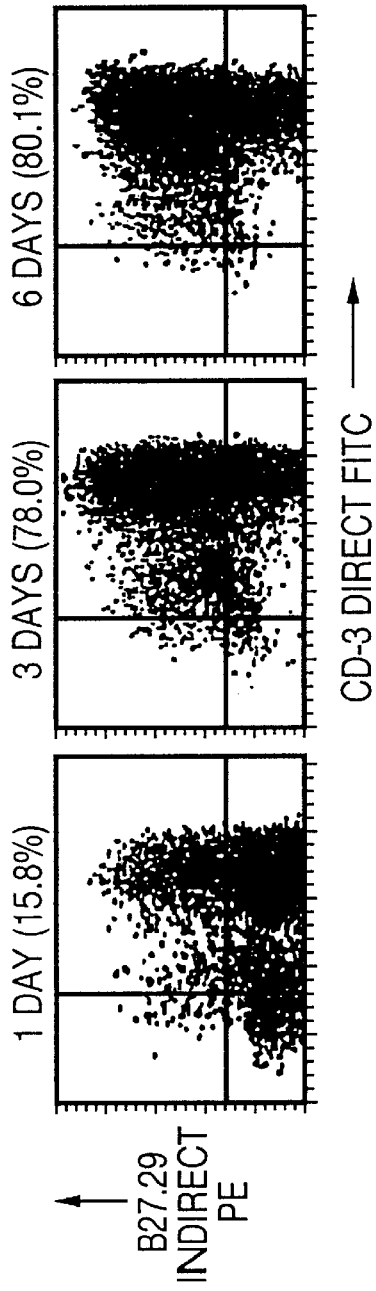
Figure 2:
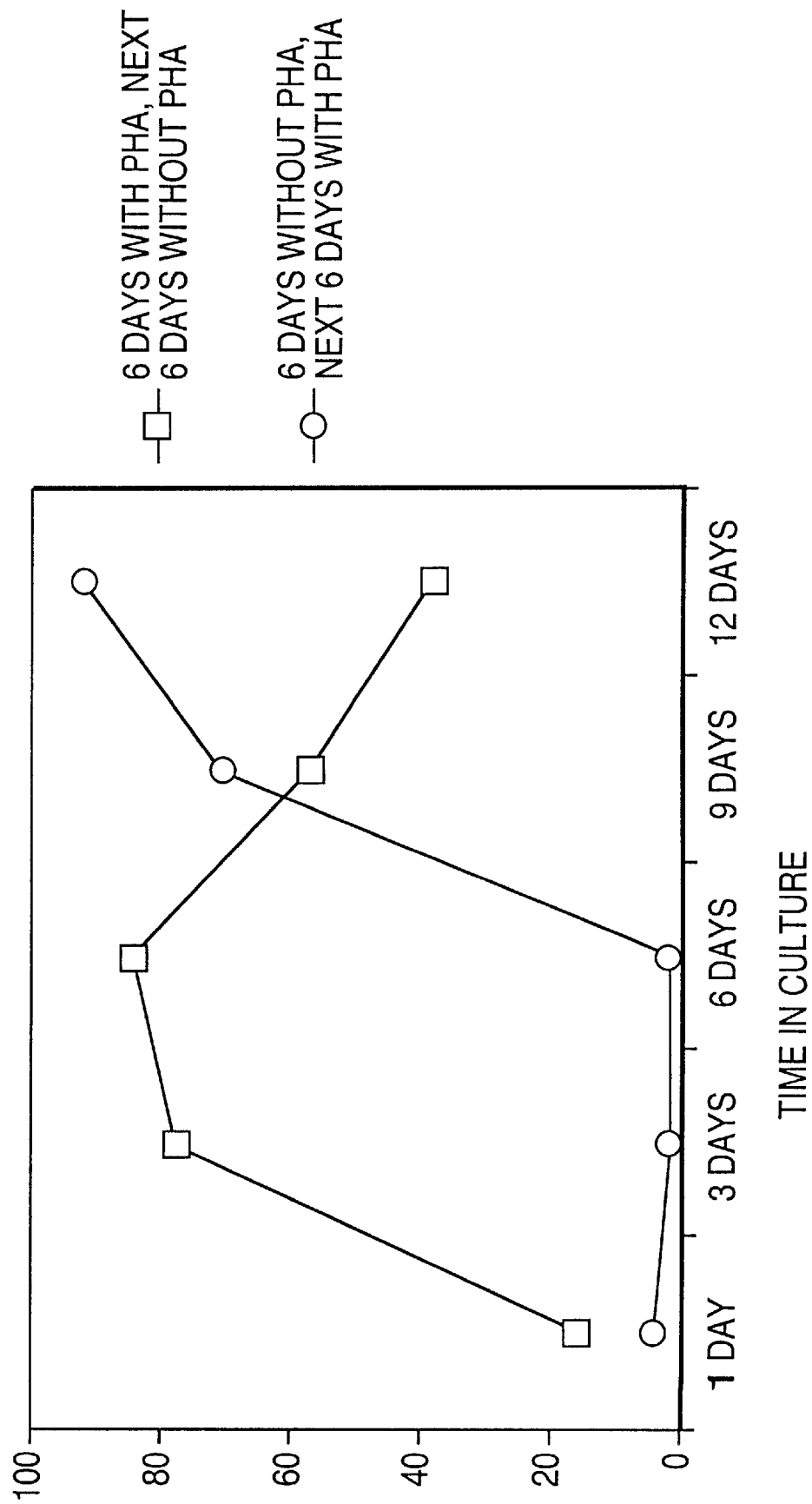
FIG. 2 demonstrates that expression of MUC-1 mucin on T-cells is reversible, as measured by MUC-1-specific antibody. Squares: Peripheral blood lymphocytes (PBLs) were cultured in the presence of phytohemagglutanin (PHA) for 1, 3 and 6 days. At day 6, the cells were washed, harvested and recultured in the absence of PHA (media alone) for further 3–6 days. Circles: PBLs were cultured in the absence of PHA for 6 days after which PHA was added and cells were cultured again for a further 6 days.

The present invention derives from the surprising observation that MUC-1, which heretofore was thought to be biologically important only in the context of certain disease states, plays a key role in the normal immunological response. Thus, when peripheral T-cells isolated from normal human blood, i.e., from non-cancerous patients, were monitored for the presence of MUC-1, only about 3–4% of these were found to express MUC-1. In contrast, upon mitogenic stimulation, approximately 80% of this same population of T-cells expressed MUC-1. This clearly shows a correlation between T-cell activation and MUC-1. These data are provided in more detail below in the Examples.

As set out in detail below, MUC-1 mucin probably is involved in normal immune regulation, more specifically in T-cell activation/inactivation. Evidence supporting this conclusion includes: [1] newly synthesized MUC-1 mucin is rapidly induced and appears on the cell surface of the majority of activated human T-cells; [2] the down regulation of MUC-1 mucin expression after the mitogenic stimulus is removed; [3] anti-MUC-1 mAb B27.29 (MUC-1-specific) inhibits the T-cell proliferative response; [4] new expression of MUC-1; [5] MUC-1 mucin is either shed or secreted into the supernatants of cultures of phytohemaglutanin (PHA) activated human T-cells; [6] soluble large molecular weight MUC-1 mucin inhibits T-cell proliferation and induces an anergy-like state that is reversible by IL-2 or anti-CD28 antibody; and small molecular weight MUC-1 reverses MUC-1 -induced anergy. Agrawal el at, Nature Med. 4:43 (1998).

This conclusion also explains certain observations from the art that suggest normal functions for MUC-1. Specifically, it unifies the observations that: certain endometrial MUC-1 glycoforms vary during the menstrual cycle; progesterone up regulates the transcription of MUC-1, maximumally during implantation; and the association of high levels of progesterone during days 14–28 of the menstrual cycle with inhibition of cytotoxic T-cell (CTL) activity in the uterus. Since MUC-1 is herein shown to be a negative regulator of normal T-cell activation, it is likely that MUC-1 is acting to down-regulate CTL activity which would otherwise prevent embryo implantation through CTL-mediated rejection.

Definitions

As used in this specification, an "activated T-cell" is one that is in the following phases of the cell cycle: the $G_1$ phase, the S phase, the $G_2$ phase or the M (mitosis) phase. Thus, an "activated T-cell" is undergoing mitosis and/or cell division. An activate T-cell expresses cell surface activation markers, intracellular activation signalling molecules/cytokines, but are not yet dividing. An activated T-cell may be a T helper ($T_H$) cell or a cytotoxic T-cell (cytotoxic T lymphocyte (CTL or $T_c$)). Activation of a naive T-cell is initiated, for example, by exposure of such a cell to an antigen presenting cell (APC) (which contains antigen/MHC complexes) and to a molecule such as IL-1. The antigen/MHC complex interacts with a receptor on the surface of the T-cell (T-cell receptor (TCR)). Golub et al., eds. IIMMUNOLOGY: A SYNTHESIS, Chapter 2: "The T-cell Receptor" (1991). The skilled artisan will recognize that suitable accessory molecules may also be involved in activation of T-cells. Examples of such accessory molecules include B7.1 (binds to CD28); B7.2 (binds to CD28); and ICAM-1 (binds to LFA-1).

As used in this specification "memory T-cells," also known as "memory phenotype" T-cells, is used to designate a class of T-cells that have previously encountered an antigen but are now resting and are capable of being activated. Memory T-cells are T-cells which have been exposed to antigen and then survive for extended periods in the body without the presence of stimulating antigen. However, these memory T-cells respond to "recall" antigens. In general, memory T-cells are more responsive to a "recall" antigen, when compared with the naive T-cell response to antigen. Memory cells can be recognized by the presence of certain cell-surface antigens, such as CD45R0, CD58, CD11α, CD29, CD44 and CD26, which are markers for differentiated T-cells.

As used herein, the terms "anergy" and "immunosuppression" are used interchangeably and specifically incorporate all attributes ascribed to these terms, individually and collectively, by the immunological arts. Moreover, these terms are also used in some instances to denote the normal negative functions of MUC-1 that down-regulate the immune response.

MUC-1 "antagonists" or "inhibitors," as used generically herein, specifically include inhibitors MUC-1 function, like competitive inhibitors and MUC-1 specific antibodies.

The term "treating" in its various grammatical forms in relation to the present invention refers to preventing, curing, reversing, attenuating, alleviating, minimizing, suppressing or halting the deleterious effects of a disease state, disease progression, disease causative agent or other abnormal condition.

Measuring T-cell Activation

One aspect of the invention provides a method of determining whether a T-cell is activated. A typical method involves detecting the amount of MUC-1 expression in a T-cell-containing sample and comparing the amount of MUC-1 expression to a non-activated T-cell-containing control.

The sample will be provided from a patient, who may be a human or non-human animal. Although the sample may be from any tissue origin, it typically will be derived from blood, lymph or tissue infiltrates. The sample specifically may comprise intact T-cells and/or some fraction thereof, such as protein or nucleic acid fractions. Isolated or enriched MUC-1 protein and/or messenger RNA (mRNA) are specifically included. Tissue infiltrates include samples taken from the lungs, tumors, lymph nodes, pericardium, tissue transplant site and the thoracic and peritoneal cavities. Control samples may be obtained from healthy volunteers, whereby a standardized baseline may be established.

Methods of detection include any detection system available that can be adapted to detecting MUC-1 expression. Of course, this can be accomplished by monitoring, for example, protein or mRNA levels, as discussed below. Some exemplary methods utilize antibodies for detecting the protein or polynucleotides for detecting the mRNA. Samples are generally controlled for relative numbers of T-cell by using detection agents in parallel, which detect all T-cell, or specific subsets of them. For example, antibodies directed to CD4 and/or CD8 could be used to normalize for total (when used together) or specific subsets of T-cell (used separately). In the case of kits involving detecting mRNA, known housekeeping genes can be used as a standard, since they have relatively constant levels of expression.

In a more general sense, the activation of T-cells is indicative of activation of the immune system in general. Since MUC-1 expression, transport and release from the cell surface are all increased upon T-cell activation, shed MUC-1, for example, will correlate with T-cell activation, and thus global immune activation. Hence, general immune activation may be ascertained by providing a sample from a patient who is suspected of suffering from a relevant immune alteration and measuring the amount of soluble MUC-1. In this case, the sample will preferably be T-cells derived from blood, lymph, and the like.

It is noted that the use of MUC-1 as a marker for T-cell activation is not inconsistent with its general role as an immune down-regulator. The data show that MUC-1 is only expressed by activated T-cells and it exerts its negative effect on T-cells only after it has reached the T-cell surface, presumably in sufficient quantity to induce some cross-linking. An example of a similar mechanism is CTLA-4 which acts similarly. Thus, while mRNA levels or intracellular levels of MUC-1 will probably be most useful in diagnostic applications, cell surface MUC-1 may also be used in this manner, especially if monitored over time.

Compositions and Kits for Detecting T-cell Activation

In general, the methods may be qualitative or quantitative. The qualitative methods may be adapted to assemble kits which may be used in the clinical laboratory or even the clinician's office. One such kit would contain some means for immobilizing T-cells, for instance T-cell-specific antibodies (e.g., antibody to T-cell receptors) bound to a dish or a dipstick, a solution for washing away the non-T-cell components, a MUC-1-specific antibody, and some means for detecting the MUC-1-specific antibody. One method of using the kit would include exposing the T-cell-containing sample to the immobilized T-cell-specific antibody, washing the sample to remove non-T-cell material, exposing the washed sample to MUC-1-specific antibody and detecting the MUC-1 specific antibody. The MUC-1-specific antibody can be detected, for example, by providing it in a form conjugated to an enzyme which utilizes a chromogenic substrate. Alternatively, a secondary, enzyme-linked antibody can be used. To provide for a control, prior to exposure of the sample to the T-cell-specific antibody, a white blood cell count can be done whereby a specific number of these cells is used as a sample.

Quantitative methods for detecting proteins include radioimmunoassays (RIAs), enzyme-linked immunosorbant assays (ELISAs), Western blots, fluorescence activated cell sorting (FACS), immunohistochemistry. Quantitative methods for detecting mRNA include reverse transcription-polymerase chain reaction (RT-PCR), Northern blotting, chemical (non-enzymatic) amplification reaction.

Antibodies may be labelled using a variety of techniques known to those in the field. Exemplary labels include enzymes, fluorescent markers and radionuclides. These are well known in the art.

Methods of detecting mRNA, as known in the art, have the common feature of contacting a sample with a probe which comprises a polynucleotide encoding a MUC-1-associated nucleotide sequence. MUC-1-associated nucleotide sequences include those which actually encode MUC-1 (and their complement) and sequences associated with MUC-1 expression, including introns and 5' and 3' untranslated regions. Preferred probes are situated at or near the 5' end of the gene.

The polynucleotide probes may be RNA or DNA, but they are preferably deoxyribo polynucleotides. Some more preferred polynucleotides are oligonucleotides from about 15 to about 30 nucleotides in length, most preferably about 17 to about 23 nucleotides. Probes will be based on the native MUC-1 sequence, which is known in the art.

Therapeutic Rationale

Previous observations that cancer-associated MUC-1 mucin inhibits human T-cell proliferative response (Agrawal et al., Nature Med. 4:43 (1998)) and the present data showing that MUC-1 mucin is transiently expressed on, and shed or secreted by, activated human T-cells, clearly indicates that MUC-1 mucin plays an important regulatory role in an immune response. In addition, the observations that MUC-1 mucin can present multiple functional domains e.g. anti-adhesion, pro-adhesion as well as inhibit T-cell proliferative response (Agrawal, Nature Med. 4:43 (1998); Ligtenberg et al., Cancer Res. 52:2318 (1992); Wesseling et al., J. Cell Biol. 129:255 (1995); Wesseling et al., Mol. Biol. Cell 7:565 (1996)), are further consistent with the present conclusion that MUC-1 expression on T-cells plays an important homeostatic function. In fact, it is likely that MUC-1 mucin expression in activated T-cells actively terminates T-cell responses by down regulating their proliferation and, moreover, MUC-1 may serve a role in lymphocyte trafficking due to its adhesion and/or anti-adhesion properties.

Without being bound by a particular theory, the inventors hypothesize that MUC-1 expression is essential for T-cell activation as it is synthesized and appears on the cell surface. Once on the cell surface, however, MUC-1 seems to exert its negative effects The data below suggest that the key to this negative effect is crosslinking of MUC-1 on the cell surface (and likely, thereby, crosslinking a receptor to which it binds).

MUC-1 is made up of 60 to 100 tandem repeats, which have been linked to the activity of the molecule. Prior data show that exogenously added large molecular weight MUC-1 (having many repeats) can cause T-cell inactivation, and that this can be reversed by treatment with small molecular weight MUC-1 molecules (having 1–3 repeats. If each MUC-1 repeat binds a receptor molecule on the T-cell surface, the large molecular weight versions would effectively crosslink those individual receptors. On the other hand, molecules having 1–3 repeats probably act as competitive inhibitors, competing with larger MUC-1 molecules for receptor binding sites and thereby preventing effective crosslinking of the putative MUC-1 receptor.

As T-cell activation progresses and MUC-1 accumulates to higher levels and is shed, it is believed that each molecule becomes available to interact with numerous MUC-1 receptors, which induces crosslinking and, thus, invokes the immuno-suppressing activity of MUC-1. This, however, can be induced artificially. Further, data presented below show that, while bivalent IgG anti-MUC-1 antibodies have some down-regulatory effect on T-cell activation, this can be amplified by adding a secondary antibody or by using a hexavalent IgM antibody instead. In addition, our prior experiments demonstrated that multiple tandem repeats are important for inducing T-cell inhibition by soluble MUC-1. Either way, the key to MUC-1-mediated immunosuppression seems to be crosslinking.

Accordingly, both inhibiting and promoting MUC-1 activity will be useful in treating diseases associated, on the one hand, with illegitimate or clinically premature T-cell deactivation and, on the other hand, with illegitimate T-cell activation. The former conditions are treatable using MUC-1 antagonists and the latter are treatable using MUC-1 enhancers.

The invention contemplates modulators of MUC-1 activity that fall into two categories, based on the net result of their application to a T-cell. The first category includes MUC-1 antagonists, alleviate T-cell anergy or immunosuppression and, therefore, have a net overall immuno-stimulatory effect on these cells. These inhibitors reverse the natural negative role of MUC-1, which down-regulates the immune response. Such antagonists are useful in treating patients suffering from conditions characterized by T-cell anergy or immunosuppression, and in treating any other conditions where induction of a T-cell response is desired.

The second category of MUC-1 modulators has very nearly the opposite effect of the first category. These modulators, or MUC-1 enhancers, rather than antagonising the negative effects of MUC-1, actually facilitate them. In other words, they enhance MUC-1-induced down-regulation of the immune response and, thereby, they induce anergy or immunosuppression; they are generally immunosuppressive.

MUC-1 Antagonists

As indicated, one class of MUC-1 modulators include antagonists of MUC-1. Some MUC-1 antagonists interfere with the binding of MUC-1 to its surface receptor, thereby disrupting the crosslinking required for the negative effects of MUC-1. MUC-1 antagonists generally act by binding either MUC-1 or its receptor, but in all cases they prevent MUC-1-mediated immunosuppression, probably by preventing cross-linking. This disruption can occur, for example, by competitively inhibiting the binding of MUC-1 to its receptor.

The antagonists can be derived from the MUC-1 molecule itself, and they can be MUC-1 peptide derivatives, based on the native MUC-1 core repeat sequence. In one embodiment, the peptide would include portions of the extracellular tandem repeat region of MUC-1, which includes repeats of the amino acid sequence (SEQ ID NO: 2) DTRP (Asp-Thr-Arg-Pro). Preferably these tandem repeats include the sequence (SEQ ID NO: 3) SAPDTRP (Ser-Ala-Pro-Asp-Thr-Arg-Pro).

A MUC-1 "core repeat," "core sequence" or "MUC-1 core" as used herein generally refers to that present in the native MUC-1 molecule, which comprises the 20 amino acid sequence (SEQ ID NO: 1) PDTRPAPGSTAPPAHGVTSA (Pro-Asp-Thr-Arg-Pro-Ala-Pro-Gly-Ser-Thr-Ala-Pro-Pro-Ala-His-Gly-Val-Thr-Ser-Ala), and derivatives of this sequence. Thus, different permutations of the 20 amino acid core sequence may be used, including substitutions, deletions, other permutations, and multiple repeats of any of the foregoing. For example, conserving the basic amino acid order and size of the peptide, the starting residue may be permuted. In one example, the repeat may begin with (SEQ ID NO: 4) GVTSA, instead of PDTRP, for example, yielding (SEQ ID NO: 6) GVTSAPDTRPAPGSTAPPAH. Other, similar permutations are also possible where the single repeat is linearly permuted by simply beginning with a different amino acid.

Deletion derivatives of this core, including truncations and internal deletions, are especially useful. One particularly useful MUC-1 peptide derivative of this class is a 16 amino acid peptide of the sequence (SEQ ID NO: 7) GVTSAPDTRPAPGSTA.

Some preferred peptide-based MUC-1 derivatives comprise one, or less than one, peptide core repeat of the MUC-1 mucin. Derivatives having less than one repeat generally contain at least 6 amino acids and even more preferably at least ten. This, of course, is subject to such a molecule having the requisite anergy/immunosuppression alleviating properties. The maximum size of "at most one MUC-1 core repeat" would be 20 amino acids, as prescribed by the native length. Hence the most preferred length is about ten to about twenty amino acids.

Further MUC-1 derivatives include modified versions of a single MUC-1 core repeat. For example, given the basic repeat sequence, conservative substitutions may be made which preserve the requisite immunostimulatory characteristics. Such conservative substitutions include: charged amino acid for, preferably similarly, charged amino acid substitutions; polar for polar substitutions; and hydrophobic for hydrophobic substitutions. Substitutions may also rationally be made on the basis of physical characteristics such as size and ability to form or break helices. For example, proline and glycine may be substituted for one another based on their common helix-breaking properties.

Other substitutions include replacing the L-amino acid with the corresponding D-amino acid. This rationale, moreover can be combined with the foregoing conservative substitution rationales. For example, D-serine may be substituted for L-threonine. In addition, peptides may be prepared which have an inverse sequence, relative to the native sequence. Hence, (SEQ ID NO: 2) DTRP becomes (SEQ ID NO: 5) PRTD. Such "retro-inverso" peptides are expected to have improved properties, such as increased in vivo half-life. This translates into smaller doses and more economically viable production.

Other useful MUC-1 antagonists include glycosylated or non-glycosylated peptides. Glycosylation may improve circulating half-life and allow modulation of the immunosuppression-reversing characteristics of MUC-1 derivatives. Glycosylation can be biological or non-biological. For example, biologically relevant N- or O-linked carbohydrates are envisioned. Other chemical modifications, such as succinylation are also contemplated. These specifically include modification with polyethylene glycols.

MUC-1 antagonists also specifically include multiple repeats of any of the specific MUC- I derivatives defined herein. Moreover, each of the foregoing derivatives can be mixed and matched with each other. These multiple repeats are preferably tandem and usually will have a maximum of three repeated units. Thus, for example, a multiple repeat containing the full 20 amino acid core sequence would have a maximum length of 60 amino acids. However, the maximum number of repeated units ultimately will be determined by the derivative's immunostimulatory character.

Although small peptides may be preferable from both economic and certain technical perspectives, larger molecules are also contemplated. Thus, MUC-1 antagonists may be combined with other useful therapeutic agents, yielding enhanced properties. They may be so combined, for example, covalently or electrostatically. Ideally these other therapeutic agents will be immunomodulators, and preferably will have immunostimulatory properties. Although non-protein agents are contemplated, the additional therapeutic agents are preferably proteins, which generically include peptides. Some particularly useful protein therapeutics include cytokines.

In one example, fusion proteins comprise an inventive peptide fused to a cytokine.

Such fusions are expected to have hybrid properties of reversing MUC-1-induced immunosuppression and more broadly inducing the immune response. Moreover, due to the interaction of the MUC-1-based peptide component with suppressed T-cells, the cytokine will be in a close physical proximity with the target cell, which may allow a specific cytokine-mediated induction of the very cells being de-repressed by the peptide portion of the MUC-1 derivative. Not only will immunosuppression be relieved, specific immunostimulation of the same T-cell population will be achieved.

Particularly useful cytokines include those with immunostimulatory activity. Some preferred cytokines include the interleukins (ILs), and especially IL-2. Other useful cytokines include, for example, IL-1, IL-4, IL-7, IL-10, IL-12, and γ-interferon.

Specific useful MUC-1 antagonists can be derived from purified MUC-1, or portions thereof, produced by native sources or recombinant DNA methodology, by methods that include digestion with enzymes such as pepsin or papain. Alternatively, peptides encompassed by the present invention can be synthesized using an automated peptide synthesizer such as those supplied commercially by Applied Biosystems, Multiple Peptide Systems and others, or they may be produced manually, using techniques well known in the art. See Geysen et al., *J. Immunol. Methods* 102: 259 (1978). Glycosylated and other forms of peptide or protein MUC-1 derivatives may be made according to methods well known in the art.

Although most preferred MUC-1 antagonists are protein- (or peptide-) based, other derivatives are contemplated. For example, small molecules which are amino acid or peptide mimetics may be useful. Rational design of such molecules is possible using methods known in the art. Using, for example, space-filling models, otherwise structurally unrelated compounds may be made to mimic protein-based MUC-1 derivatives. The usefulness of these MUC-1 derivatives can be confirmed using routine assays, such as those presented in Agrawal et al., Nature Medicine, 4:43 (1998).

Further MUC-1 antagonists include normal ligands of MUC-1. Especially preferred among these ligands are cell adhesion molecules, such as intracellular adhesion molecule-1 (ICAM-1). In addition, these ligands may be shorter, for example proteolytically or recombinantly produced, truncated versions or fragments. They should, however, retain the ability to bind MUC-1.

Still another important class of MUC-1 antagonists is antibody-based. Antibodies raised against the MUC-1 and its fragments are specifically contemplated. In order to act as antagonists of MUC-1 inhibitory function, antibodies should not induce crosslinking of MUC-1 and/or its cell surface receptor. Therefore, antibody antagonists of MUC-1 typically will be monovalent, such that each antibody can bind only a single MUC-1 molecule.

MUC-1 antagonists are useful in methods for treating, preventing or substantially alleviating a variety of maladies, including cancer-associated immunosuppression, induction of anergy, viral diseases, and autoimmune diseases.

Many viral diseases are known to promote some degree of immunosuppression which presumably affords them protection from immune clearance. For example, Epstein Barr Virus (EBV) induces expression of the lymphokine IL-10, which is known to down-regulate the T-cell response. Similarly, in some cases IL-4 may inhibit the TH1 response and thus shift the immune response to an antibody (humoral) response In addition, many cancers are known to mediate suppression of the T-cell response. For example, when tumors are isolated, specific T-cells called tumor infiltrating lymphocytes (TILs) are present. Although TILs are specific to the tumor from which they are isolated, they are anergic and thus do not respond to the tumor. This anergy may be reversed with interleukin-2 (IL-2) treatment.

Similarly, tumors, such as adenocarcinomas, which secrete MUC-1 induce T-cell suppression or anergy. This effect is reversed by certain molecules which likely antagonize the binding of MUC-1 to its cognate cell surface receptor. Finally, many treatment protocols, for example, for cancer and antirejection are also immunosuppressive, and MUC-1 antagonists should be equally useful as an adjunct to those therapies.

MUC-1 Enhancers

Enhancers of MUC-1 function are also contemplated as a useful part of the invention. As explained, these molecules promote the T-cell down-regulatory aspects of MUC-1 function. In effect, they speed up the process of de-activating T-cells and, thus, they are immunosuppressive.

MUC-1 enhancers generally Will induce crosslinking of MUC-1 molecules and/or MUC-1 receptors on the cell surface. Accordingly, they share the common characteristic of specifically binding MUC-1 and/or its receptor and they usually have multiple binding sites per molecule, in order to induce the crosslinking needed for immunosuppression. Due to these desirable characteristics, antibodies and their derivatives are preferred MUC-1 enhancers. Moreover, polyvalent versions, like hexavalent IgMs, are preferred because they should have a higher suppressive potential. On the other hand, where monovalent or bivalent molecules, like IgG and certain antibody derivatives, are employed, secondary antibodies may be necessary to induce sufficient crosslinking. Of course, secondary antibodies also may be used with higher-order molecules, but the are less likely to be needed in such a context.

MUC-1 enhancers may be used to treat a variety of disorders characterized by over-active immune function, like autoimmune disorders and inflammatory disorders. MUC-1 enhancers may also be used to prevent or suppress organ transplantation rejection and graft versus host disease in bone marrow transplantation. They may also be used in conjunction with other known compounds that are useful for the same purposes.

As used herein, an "inflammatory disorder" refers to any of the many inflammatory disorders that are well known to those of skill in the art. These disorders include, but are not limited to, the following disorders: inflammatory arthritis such as rheumatoid arthritis, psoriasis, allergies such as allergic contact dermatitis, and ankylosing spondylitis.

As used herein, an "autoimmune disorder" refers to any of the many autoimmune disorders that are well known to those of skill in the art. These disorders include, but are not limited to, the following disorders: myasthenia gravis, systemic lupus erythematosus, polyarteritis nodosa, Goodpastures syndrome, isopathic thrombocytopenic purpura, autoimmune hemolytic anemia, Grave's disease, rheumatic fever, pernicious anemia, insulin-resistant diabetes mellitus, bullous pemphigold, pemphigus vulgaris, viral myocarditis (Cocksakie B virus response), autoimmune thyroiditis (Hashimoto's disease), male infertility (autoimmune), sarcoidosis, allergic encephalomyelitis, multiple sclerosis, Sjorgens disease, Reiter's disease, Celiac disease, sympathetic ophthalmia, and primary biliary cirrhosis.

MUC-1-based Antibodies and Antibody Fragments

Antibodies are useful in generating reagent for detection of activated T-cells and in producing either MUC-1 antagonists or MUC-1 enhancers. Antibodies include, but are not limited to polyclonal antibodies, monoclonal antibodies (mAbs), humanized or chimeric antibodies, single chain antibodies including single chain Fv (scFv) fragments, Fab fragments, F(ab')$_2$ fragments, fragments produced by a Fab expression library, anti-idiotypic (anti-Id) antibodies, epitope-binding fragments, and humanized forms of any of the above.

In general, techniques for preparing polyclonal and monoclonal antibodies as well as hybridomas capable of producing the desired antibody are well known in the art (Campbell, A. M., *Monoclonal Antibody Technology: Laboratory Techniques in Biochemistry and Molecular Biology*, Elsevier Science Publishers, Amsterdam, The Netherlands (1984); St. Groth et al., *J. Immnol. Methods* 35:1–21 (1980); Kohler and Milstein, *Nature* 256:495–497 (1975)), the trioma technique, the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96). Affinity of the antisera for the antigen may be determined by preparing competitive binding curves, as described, for example, by Fisher, Chap. 42 in: *Manual of clinical Immunology*, second edition, Rose and Friedman, eds., Amer. Soc. For Microbiology, Washington, D.C. (1980).

Fragments or derivatives of antibodies include any portion of the antibody which is capable of binding MUC-1. Antibody fragments specifically include F(ab')$_2$, Fab, Fab' and Fv fragments. These can be generated from any class of antibody, but typically are made from IgG or IgM. They may be made by conventional recombinant DNA techniques or, using the classical method, by proteolytic digestion with papain or pepsin. See CURRENT PROTOCOLS IN IMMUNOLOGY, chapter 2, Coligan et al., eds., (John Wiley & Sons 1991–92).

F(ab')$_2$ fragments are typically about 110 kDa (IgG) or about 150 kDa (IgM) and contain two antigen-binding regions, joined at the hinge by disulfide bond(s). Virtually all, if not all, of the Fc is absent in these fragments. Fab' fragments are typically about 55 kDa (IgG) or about 75 kDa (IgM) and can be formed, for example, by reducing the disulfide bond(s) of an F(ab')$_2$ fragment. The resulting free sulfhydryl group(s) may be used to conveniently conjugate Fab' fragments to other molecules, such as detection reagents (e.g., enzymes).

Fab fragments are monovalent and usually are about 50 kDa (from any source). Fab fragments include the light (L) and heavy (H) chain, variable ($V_L$ and $V_H$, respectively) and constant ($C_L$ $C_H$, respectively) regions of the antigen-binding portion of the antibody. The H and L portions are linked by an intramolecular disulfide bridge. Because they are monovalent, and thus will not induce crosslinking, Fab fragments (like Fv, SCFv and other monovalent species) are particularly useful as antagonists of MUC-1 function.

Fv fragments are typically about 25 kDa (regardless of source) and contain the variable regions of both the light and heavy chains ($V_L$ and $V_H$, respectively). Usually, the $V_L$ and $V_H$ chains are held together only by non-covalent interacts and, thus, they readily dissociate. They do, however, have the advantage of small size and they retain the same binding properties of the larger Fab fragments. Accordingly, methods have been developed to crosslink the $V_L$ and $V_H$ chains, using, for example, glutaraldehyde (or other chemical crosslinkers), intermolecular disulfide bonds (by incorporation of cysteines) and peptide linkers. The resulting Fv is now a single chain (i.e., SCFv).

Other antibody derivatives include single chain antibodies (U.S. Pat. No. 4,946,778, Bird, *Science* 242:423–426 (1988); Huston et at., *Proc. Natl. Acad. Sci. USA*

85:5879–5883 (1988); and Ward et al, Nature 334:544–546 (1989)). Single chain antibodies are formed by linking the heavy and light chain fragments of the Fv region via an amino acid bridge, resulting in a single chain FV (SCFv).

Derivatives also include "chimeric antibodies" (Morrison et al., *Proe. Natl. Acad. Sci.*, 81:6851–6855 (1984); Neuberger et al., *Nature*, 312:604–608 (1984); Takeda et al, *Nature*, 314:452–454 (1985)). These chimeras are made by splicing the DNA encoding a mouse antibody molecule of appropriate specificity with, for instance, DNA encoding a human antibody molecule of appropriate specificity. Thus, a chimeric antibody is a molecule in which different portions are derived from different animal species, such as those having a variable region derived from a murine mAb and a human immunoglobulin constant region. These are also known sometimes as "humanized" antibodies and they offer the added advantage of at least partial shielding from the human immune system. They are, therefore, particularly useful in therapeutic in vivo applications.

Pharmaceutical Compositions of the Invention

The inventive compositions may be formulated for administration in a variety of ways. The pharmaceutical compositions of the invention generally contain a pharmaceutically effective amount of an inventive compound. Preferably, the compound is admixed with a pharmaceutically effective vehicle (excipient).

A suitable formulation will depend on the nature of the specific medicament chosen, whether the treatment is in vivo or ex vivo, the route of administration desired and the judgement of the attending physician. Suitable formulations and pharmaceutically effective vehicles, can be found, for example, in REMINGTON'S PHARMACEUTICAL SCIENCES, chapters 83–92, pages 1519–1714 (Mack Publishing Company 1990) (Remington's), which are hereby incorporated by reference.

Preferred vehicles include liposomes. See, for example, Remington's at 1691–92. Thus, the inventive compositions may also be formulated, and administered, in combination with other known medicaments, which may provide complementary anergy/immunosuppression relieving activity, in liposomal formulations. Preferred other medicaments include immunomodulators, such as the cytokines discussed above.

The pharmaceutical compositions of the invention also may be formulated with stimulatory antigens, such as adjuvants. Such adjuvants are well known in the vaccine arts and typically function to enhance the immune response. Thus, preferred adjuvants useful in the invention are characterized by enhancing the ability of the inventive medicaments described herein to relieve antigen-induced immunosuppression/anergy. Some examples of well-known and useful adjuvants include those derived from bacterial lipopolysaccharides, such as lipid A, monophosphoryl lipid A.

Therapeutic Methods of the Invention

The inventive therapeutic methods generally utilize the MUC-1 modulators identified above. As indicated, the antagonists and the enhancers may be used to treat different disease states, depending upon the associated immune activation state. In general, methods entail modulating the immune either using an antagonist to stimulate it or using an enhancer to suppress it.

Therapeutic methods involve administering to a subject in need of treatment a therapeutically effective amount of an inhibitor, as described above. Some methods also contemplate combination therapy. In the case where immunostimulation is desired, antagonists may be administered in conjunction with at least one other immunostimulatory medicament, and where immunosuppression is desired, enhancers may be administered with other immunosuppressants. The patient may be a human or non-human animal. A patient typically will be in need of treatment when suffering from a disorder associated with abnormal or undesirable immunosuppression or immune activation.

The inventive methods may be employed in vivo or ex vivo. In a typical ex vivo method, for example, peripheral T-cells may be isolated from patients, treated with at least one MUC-1 modulator, alone or in combination, and reinfused into the patient.

Administration during in vivo treatment may be by any number of routes, including parenteral and oral, but preferably parenteral. Specific preferred routes include direct injection of an antagonist into the tumor or the draining lymph nodes, in the case of a MUC-1-associated neoplasia. Thus, for example, the tumor infiltrating lymphocytes within the tumor, which are known to be immunosuppressed, will be specifically targeted and de-repressed.

MUC-1 modulators may be administered alone, in combination with each other, or in combination with other medicaments. Ideally these other medicament agents will be immunomodulators, and have either immunostimulatory or immunosuppressive properties. Both protein and non-protein agents are contemplated. Some particularly useful protein-based immunostimulatory agents include stimulatory antigens and cytokines. Some preferred cytokines include the interleukins (ILs), and especially IL-2. Other useful stimulatory cytokines include, for example, IL1, L-4, IL-7, L-10, IL-12, andy-interferon. For example, cytokines may be coadministered, simultaneously or in succession, with MUC-1 antagonists. Of course, MUC-1 inhibitors also may be used in combination with other immunostimulatory regimens. Immunosuppressive agents that may be coadministered with MUC-1 modulators include steroid hormones, non-steroidal antiinflammatories, corticosteroids, and even cytoablative agents.

Determining a pharmaceutically effective amount MUC-1 inhibitor is well within the purview of the skilled clinician, and largely will depend on the exact identity of the inhibitor, particular patient characteristics, route of administration and the nature of the disorder being treated. General guidance can be found, for example, in the publications of the International Conference on Harmonisation and in REMINGTON'S PHARMACEUTICAL SCIENCES, chapters 27 and 28, pp. 484–528 (Mack Publishing Company 1990).

Determining a pharmaceutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, is measured by alleviation or substantial alleviation of anergy/immunosuppression or unwanted/illegitimate T-cell activation, in accord with the definition of "treating" discussed above.

U.S. Provisional Application No. 60/090,916 is hereby incorporated by reference in its entirety.

EXAMPLES

Example 1

Materials and Methods

A. Antibodies/Reagents

Mouse IgG, goat IgG and MOPC.21 (IgG1), were obtained from Sigma (Mississauga, Ontario, Canada). The cell culture media RPMI-1640, fetal bovine serum (FBS) and AIM V were obtained from Gibco BRL (Burlington, Ontario, Canada). Anti-CD3-FITC, anti-CD4-FITC/CD8-PE, IgG1-FITC/IgG1-PE, leukogate (CD45-FITC/CD14-PE), IgG1-FITC/IgG2-PE simultest control, anti-CD25-PE and anti-CD69-PE were purchased from Becton & Dickinson (San Jose, Calif., USA). Goat anti-mouse IgG1-PE, IgG1-FITC and isotype control mouse IgG1 were obtained from Southern Biotech (Birmingham, Ala., USA). Ficoll-Hypaque was obtained from Pharmacia Biotech (Baie d'Urfe, Quebec, Canada). Anti-CD3 (OKT3) was used as purified antibody obtained from culture supernatant of clones purchased from American Type Culture Collection (ATCC; Rockville, Md., USA). Anti-human- MUC-1 mAb B27.29 was purified from culture supernatant of the cell line B27.29 (Reddish et al., 1992 J. Tumor Marker Oncol. 7:19).

B. Cell Surface Immunofluorescence Staining

Peripheral blood lymphocytes (PBLs) were isolated from buffy coats obtained from normal healthy donors (Canadian Red Cross, Edmonton, Alberta, Canada). For detection of cell surface antigens, PBLs cultured as indicated in each experiment were stained essentially as previously described (Agrawal e al., J. Immunol. 157:3229 (1996). Anti-MUC-1 mAb B27.29 (2 $\mu$g/5×10$^5$ T-cells) or isotype control antibody B80.3 (2 $\mu$g/5×10$^5$ T-cells) were used with indirect labelling with FITC or PE conjugated second antibody (G$\alpha$M IgG1). In parallel, appropriate isotype control antibody was always used to stain the cells in a similar way. The isotype control groups had <2% positive cells. The samples were analyzed by flow cytometry using FACSort® (Becton & Dickinson). Percent positive cells were defined as the fraction of cells exhibiting fluorescence intensities beyond a region set to exclude at least 98% of the control isotype matched antibody stained cells.

C. Proliferation Assay

PBLs were stimulated with PHA (1 $\mu$g/ml) for 3 days, T-cells were then harvested and recultured in the presence or absence of OKT3, B27.29 mAb, isotype control mAb B80.3 and Goat anti-mouse in 96 well plates in quadruplicate. On the third day, the wells were pulsed with 1 uCi/well $^3$H Thymidine (Amersham). Incorporation of $^3$H Thymidine into DNA of proliferating T-cells was measured after harvesting the plates after 18–24 h and counting in liquid scintillation counter (Beckman LS 60001C, Mississauga, ON, Canada).

D. Determination of mRNA for Human MUC-1 by PCR

MUC-1 mRNA in the lymphocytes was analyzed using reverse transcription PCR (RT-PCR). Total RNA was extracted from the T-cells using Trizol according to manufacturer's instructions (Life Technologies) and was reverse transcribed into cDNA with M-MLV Reverse Transcriptase and oligo d(T) (Perkin Elmer, Norwalk, Conn.). Subsequent DNA amplification was performed in the same tubes using AmpliTaq DNA polymerase (Perkin Elmer, Norwalk, Conn.) and MUC-1 specific primers (5'-TCTACTCTGGTGCACAACGG-3' (SEQ ID NO: 10) and 5'-TTATATCGAGAGGCTGCTTCC-3' (SEQ ID NO: 11). These primers spanned a region within the genomic DNA that contained 2 introns and would result in the amplification of a 489 bp fragment from RNA and a 738 bp fragment from any contaminating genomic DNA. MCF-7 (human breast cancer cell line obtained from ATCC) RNA was used as a positive control and mouse spleen RNA was used as a negative control. RNA specific primers for human beta actin were used as a positive control with each RNA sample. Amplified fragments were run on a 2% agarose gel. All samples from lymphocytes that had been stimulated with PHA, produced a fragment of approximately 489 bp indicating the presence of human MUC-1 mRNA. Samples from unstimulated lymphocytes produced either no fragment or a faint product upon gel electrophoresis indicating no MUC-1 message or only a small amount.

E. Determination of Soluble MUC-1 Mucin in Cell Supernatants

MUC-1 in cell culture supernatants was determined with a sandwich enzyme immunoassay (EIA) employing mAb B27.29 (Biomira Inc.) as solid phase on polystyrene microwells (Nunc Maxisorp™), horseradish peroxidase (HRP, Boehringer Mannheim), conjugated mAb B27.29 as tracer, and tetramethylbenzidine (TMB, Biomira Diagnostics Inc., Toronto, Ontario, Canada) as substrate. The HRP-B27.29 conjugate was prepared with the heterobifunctional cross-linker Sulfo-SMCC (Pierce). The EIA was calibrated by correlation with the TRUQUANT®BR™ RIA (Biomira Diagnostics Inc.). Cell culture supernatants were assayed undiluted; under these conditions the lower limit of detection is estimated to be in the range of 0.01–0.02 Units/ml.

Example 2

MUC-1 Mucin is Expressed on the Surface of Mitogen Activated Human T-cells

PBLs obtained from buffy coats of normal Red Cross donors were stimulated with PHA for various time periods. Expression of MUC-1 mucin on the surface of PHA activated T-cells was examined by flow cytometry using anti-MUC-1 monoclonal antibody B27.29. MUC-1 mucin expression was examined at 1 day, 3 days and 6 days after in vivo culture initiation with or without PHA stimulation. FIG. 1, presents the time course of MUC-1 expression on activated human T-cells. At each time point, cells were collected and stained for CD3 and MUC-1 expression. The top (A) row represents cells in the absence of mitogen stimulus and the bottom (B) row represents cells cultured in the presence of PHA. As controls isotype matched antibody was used (data not shown), that stained <2% of the cells. The number in parentheses represents percent MUC-1 positive T-cells.

FIG. 1 demonstrates that in cultures without added PHA there was a low (1–4%) number of MUC-1 positive cells in the CD3$^+$ T-cell population. In PHA stimulated cultures there was an increase in the number of B27.29$^+$ CD3$^+$ cells to a peak of approximately 80% positive cells 3 to 6 days post culture initiation. As a control for mAb B27.29 binding specificity, we determined whether the presence of soluble MUC-1 mucin inhibits mAb B27.29 binding to 3 day PHA activated T-cells. We observed a MUC-1 mucin dose dependent inhibition of staining of activated human T-cells with B27.29: at 1 $\mu$g of MUC-1 mucin, a 25% inhibition of binding was noted, at 10 $\mu$g MUC-1 a 45% inhibition and at 50 $\mu$g MUC-1 a 65% inhibition of B27.29 binding to activated T-cells was noted. A negative control mucin (OSM) did not inhibit binding of B27.29 to PHA activated T-cells (0% inhibition of binding of mAb B27.29 at 50 $\mu$g OSM).

Example 3 mRNA for MUC-1 Mucin is Present in Activated T-cells

In order to confirm that the appearance of cell surface MUC-1 on activated T-cells represents the presence of newly synthesized mucin, RT-PCR was performed in a time course experiment where the expression of MUC-1 on the cell surface was determined at the same time as MUC-1 mRNA determination. Both MUC-1 mRNA and surface expression were determined in T-cells cultured in the presence or absence of PHA after 1 day, 3 day and 6 days after culture. Gel electrophoresis demonstrated that MUC-1 specific mRNA could be detected by RT-PCR after 24 h of PHA stimulation with increased expression noted at days 3 and 6. MUC-1 mRNA was present in PHA stimulated cells but not in the unstimulated cells and correlated with surface expression of MUC-1 (see FIG. 1).

Example 4
MUC-1 Mucin is Expressed by both CD4 and CD8 Positive T-cells

Double staining with anti-CD4 or anti-CD8 mAbs and mAb B27.29 demonstrates that at days 5 and 7 after activation of PBLs with PHA, approximately 80% of the CD4$^+$ T-cells are MUC-1 positive and approximately 65% of the CD8$^+$ T-cells are MUC-1 positive (Table I).

TABLE I

MUC-1 is expressed on both CD4$^+$ and CD8$^+$ T-cells

| Time after PHA Stimulation | % of CD4$^+$ T-cells positive for MUC-1 | % of CD8$^+$ T-cells positive for MUC-1 |
|---|---|---|
| 5 days | 86.6% | 69.6% |
| 7 days | 80.7% | 66.5% |

Example 5
MUC-1 Mucin is Co-expressed with other T-cell Activation Markers

Double staining for MUC-1 mucin expression with anti-CD25 or anti-CD69 mAbs was carried out on days 1, 3, 6 following T-cell activation with PHA. Table II demonstrates that the percentage of cells co-expressing CD69 or CD25 and MUC-1 mucin increased with time in culture. However, the kinetics of CD69 or CD25 expression seems to be different than that of MUC-1 expression because at day 1 after stimulation approximately 18% of the CD25$^+$ T-cells are MUC-1 positive and 15% of the CD69$^+$ T-cells are MUC-1 positive; at day 3 after stimulation approximately 74% of the CD25$^+$ T-cells are MUC-1 positive and 75% of the CD69$^+$ T-cells are positive; finally, at day 6 after stimulation approximately 80% of both CD25$^+$ and CD69$^+$ T-cells are MUC-1 positive.

TABLE II

MUC-1 coexpressed with other T-cell activation markers

| Time after PHA stimulation | % of CD69$^+$ T-cells positive for MUC-1 | % of CD25$^+$ T-cells positive for MUC-1 |
|---|---|---|
| 1 h | 9.1 | ND |
| 4 h | 8.1 | ND |
| 1 day | 14.75% | 17.4% |
| 3 days | 75.5% | 74.3% |
| 6 days | 81.6% | 80.2% |

Example 6
Down regulation of MUC-1 Expression on Activated T-cells Following Removal of the Mitogen T-cells were cultured in the presence of PHA for 1, 3 and 6 days, followed by washing and reculturing in media without PHA for an additional 3 and 6 days. FIG. 3 shows that expression of MUC-1 mucin on T-cells is reversible. (n) PBLs were cultured in the presence of PHA for 1, 3 and 6 days. At day 6, the cells were washed, harvested and recultured in the absence of PHA (media alone) for further 3–6 days. (l) PBLs were cultured in the absence of PHA for 6 days after which PHA was added and cells were cultured again for a further 6 days. In both groups, cells were harvested at each time point 1, 3, 6, 9 and 12 days and double stained for CD3 and MUC-1 (B27.29 mAb) expression. Data is shown as the mean percent of MUC-1 positive T-cells±S.D.

As shown in FIG. 3, after removing the PHA from the cultures, MUC-1 expression was reduced with time. This reduction in MUC-1 expression is analogous to transient expression of T-cell activation marker CD69 (Testi et al., J. Immunol. 142: 1854–1860 (1989)). It was found that surface CD69 expression reaches to peak level by 18–24 h after stimulation and declines with the removal of stimuli. In addition, T-cells cultured in the absence of PHA for 1, 3 and 6 days and then stimulated with PHA, MUC-1 on T-cells expression was not observed up to 6 days in culture without PHA but MUC-1 expression is apparent after subsequent.

Example 7
Soluble MUC-1 Mucin is Found in Cell Supernatants of Activated Human T-cell cultures An enzyme-linked immunoassay (EIA) specific for MUC-1 mucin was used to test supernatants from PHA activated T-cells for the presence of soluble MUC-1 mucin. Table III shows that supernatants from PHA activated but not non-activated cultures contained increasing amount of soluble MUC-1 mucin with a peak level of approximately 27 U/ml culture supernatant at day 6.

TABLE III

Activated human T-cells secrete or shed detectable amounts of MUC-1 into culture supernatants

| | Amount of secreted MUC-1 (U/mlX10$^2$) mean ± S.D. | |
|---|---|---|
| Time in Culture | PBLs without PHA | PBLs with PHA (1 ug/ml) |
| 1 day | 2.0 ± 0.1 | 1.5 ± 0.2 |
| 3 days | 1.6 ± 0.1 | 12.9 ± 1.0 |
| 6 days | 1.3 ± 0.0 | 27.2 ± 3.6 |
| 7 days | 1.7 ± 0.1 | 24.2 ± 0.1 |

Example 8
Cross-linking Surface MUC-1 Mucin by Antibody Inhibits the T-cell Proliferative Response Human PBLs were stimulated with PHA for 3 days to induce the expression of MUC-1 mucin. At this time the cells were harvested, washed, and recultured in the presence of anti-CD3 (OKT3, as polyclonal stimuli), with or without anti-MUC-1 mAb B27.29 and Goat-anti-mouse antibody. It appears that the T-cells stimulated in the presence of MUC-1 cross-linking conditions, the proliferation response was lower than that of the cells cultured in the presence of isotype control antibody. This experiment is illustrated in FIG. 4. There, human PBLs were cultured in the presence of PHA for 3 days. At this time, cells were harvested and set up in 96 well flat bottom plate at 1×10$^5$ cells/well in the presence or absence of media, OKT3 (αCD3 as stimulant), αMUC-1 (B27.29 mAb) and Goat-anti-mouse antibody. On the third day of culture, $^3$H-Tdr was added and proliferation was measured on the fourth day. The data represent mean CPM±S.D. of four replicate wells.

Example 9

Cross-linking Surface MUC-1 Mucin by Antibody Represses T-cell Proliferative Response This example shows that cross-linking of MUC-1 (and, thus, likely its cell surface receptor) is the triggering event for T-cell down-regulation. These data show that when a bivalent IgG anti-MUC-1 molecule is used, a secondary antibody is required to induce substantial suppression. On the other hand, when a hexavalent IgM antibody is used, effective down-regulation is observed without a secondary antibody.

Experiments were performed essentially as describe in Example 8. Briefly, $2 \times 10^5$ human peripheral T lymphocytes/well were stimulated with anti-CD3 (OKT3, polyclonal stimulus) in the presence of anti-MUC-1 antibody (B27.29) or the appropriate isotype control or with other antibodies along with second cross-linking goat-anti-mouse antibody for 3 days in a 96-well microtitre flat well plate. After this time, the wells were pulsed with $^3$H-Tdr overnight and the cells were harvested. Incorporation of $^3$H-Tdr in the DNA of proliferating T-cells was determined by liquid scintillation counting. The results are shown as percent inhibition of proliferation as calculated by:

$$\frac{\text{Control CPM} - \text{Experimental CPM in the Presence of Various Antibodies}}{\text{Control CPM}} \times 100$$

Data are shown in Table IV.

TABLE IV

Anti-MUC1 antibodies reactive against carbohydrate, tandem repeat peptide core or non-VNTR region, bind to activated human T-cells and induce an inhibition of proliferation.

| Antibody* | Epitope | Binding to activated T-cells (% Positive cells) | Effect on T-cell proliferation (% Inhibition) | |
|---|---|---|---|---|
| | | | 5 µg/ml** | 25 µg/ml** |
| B27.29 | Glycopeptide (VNTR) | 60–80 | 58 | 82 |
| SM3 | APDTRP (SEQ ID NO:8) (VNTR) | 54 | 26 | 96 |
| BC4E549 | TSAPDTRPAP (SEQ ID NO:9) (VNTR) | 62 | 17 | 49 |
| M29 | Non-VNTR peptide core | 28 | 24 | 48 |
| DH-1 | Le$^x$ | 49 | 9 | 59 |
| M26 | SLe$^x$ | 39 | 4 | 54 |

*Isotype matched control antibodies did not bind to activated T-cells or have an effect on T-cell proliferation.
**Antibody concentration in culture.

The foregoing detailed discussion and working examples are presented merely for illustrative purposes and are not meant to be limiting. Thus, one skilled in the art will readily recognize additional embodiments within the scope of the invention that are not specifically exemplified.

---

What is claimed is:

1. A method of determining whether a T-cell is activated, comprising contacting a T-cell-containing sample with an agent that facilitates detecting the amount of MUC-1 expression in said sample wherein said detecting comprises contacting said sample with a probe which comprises an antibody specific for MUC-1 and comparing said amount to a non-activated T-cell-containing control wherein increased levels of MUC-1 are indicative of T-cell activation.

2. A method according to claim 1, wherein said detecting comprises quantifying the amount of MUC-1 expression.

3. A method according to claim 1, wherein the probe further comprises a detectable label.

4. A method according to claim 3, wherein the label is selected from the group consisting of an enzyme, a fluorescent marker, and a radioactive label.

5. A method according to claim 1, wherein the sample is provided from a patient.

* * * * *